United States Patent [19]

Hitzel et al.

[11] 4,379,153
[45] Apr. 5, 1983

[54] BENZENESULFONYL UREAS, AND PHARMACEUTICAL PREPARATIONS

[75] Inventors: Volker Hitzel, Hofheim am Taunus; Rudi Weyer, Kelkheim; Karl Geisen, Frankfurt am Main; Günter Regitz, Bad Soden am Taunus, all of Fed. Rep. of Germany

[73] Assignee: Hoechst Aktiengesellschaft, Frankfurt am Main, Fed. Rep. of Germany

[21] Appl. No.: 211,273

[22] Filed: Nov. 26, 1980

[30] Foreign Application Priority Data

Dec. 1, 1979 [DE] Fed. Rep. of Germany ....... 2948522

[51] Int. Cl.³ .................. C07D 471/04; A61K 31/395
[52] U.S. Cl. .................................... 424/256; 546/113
[58] Field of Search ........................ 546/113; 424/256

[56] References Cited

U.S. PATENT DOCUMENTS 3,082,212  3/1963  Graf et al. ........................... 546/113
4,132,795  1/1979  Hitzel et al.

FOREIGN PATENT DOCUMENTS 1445774   1/1969  Fed. Rep. of Germany.
1670660  12/1970  Fed. Rep. of Germany.
1670700  12/1970  Fed. Rep. of Germany.
2621958  12/1977  Fed. Rep. of Germany.

OTHER PUBLICATIONS

Medicinal Chemistry, Burger, 3rd ed., Part 1, p. 77, (1970).
Labhart, Klinik der Inneren Sekretion, 3rd ed. (1978), pp. 740–742.

*Primary Examiner*—John M. Ford
*Attorney, Agent, or Firm*—Curtis, Morris & Safford

[57] ABSTRACT

Sulfonylureas of the formula

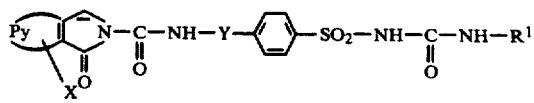

in which

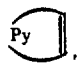

$R^1$, X and Y have the indicated meanings and the physiologically acceptable salts thereof, pharmaceutical preparations on the basis of said compounds and their use in the treatment of diabetes.

7 Claims, No Drawings

BENZENESULFONYL UREAS, AND PHARMACEUTICAL PREPARATIONS

The invention relates to sulfonylureas of the formula

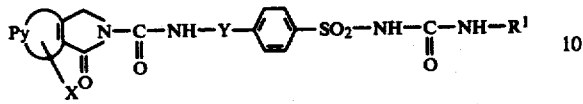

which, as such or in the form of their physiologically acceptable salts, possess blood sugar-lowering properties and are distinguished by a pronounced and long-lasting lowering of the blood sugar level so that they can be used as medicaments.

In the formula, the symbols have the following meanings:

Py 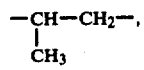:

a pyridine ring which may carry the nitrogen atom in the four possible positions, X: hydrogen, alkyl of 1 to 4 C atoms, halogen
Y: alkylene with 2-3 C atoms
$R^1$: alkyl of 4 to 8 C atoms, cycloalkyl, alkylcycloalkyl, dialkylcycloalkyl, cycloalkylalkyl, cycloalkenyl or alkylcycloalkenyl, in each case with 5-9 C atoms, methylcyclopentylmethyl, cyclohexenylmethyl, chlorocyclohexyl, methoxycyclohexyl, bicycloheptyl, bicycloheptenyl, bicycloheptylmethyl, bicycloheptenylmethyl, bicyclooctyl, nortricyclyl, adamantyl or benzyl.

In the general formula, X preferably denotes hydrogen, and methyl, especially hydrogen. Y preferably denotes —CH$_2$—CH$_2$—,

—CH—CH$_2$—,
  |
  CH$_3$ especially —CH$_2$—CH$_2$—. $R^1$ preferably denotes alkylcyclohexyl, particularly preferably 4-ethylcyclohexyl.

Suitable bicyclic radicals are: bicyclo[2.2.1]heptyl, bicyclo[2.2.1]heptylmethyl and the corresponding unsaturated radicals and bicyclo[2.2.2]octyl.

The invention further relates to processes for the manufacture of these sulfonylureas, pharmaceutical preparations which contain these or consist of these compounds, and their use for the treatment of diabetes.

The processes of manufacture are characterized in that (a) benzenesulfonyl-isocyanates, -carbamic acid esters, -thiocarbamic acid esters, -ureas, -semicarbazides or -semicarbazones, which are substituted in the 4-position by the group

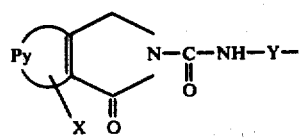

are reacted with an amine $R^1$-NH$_2$ or its salts, or sulfonamides of the formula

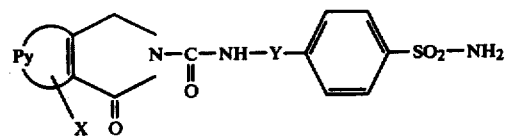

or their salts are reacted with $R^1$-substituted isocyanates, carbamic acid esters, thiolcarbamic acid esters, carbamic acid halides or ureas, (b) correspondingly substituted benzenesulfonyl-isourea ethers, -isothiourea ethers, -parabanic acids or -haloformamidines are caused to undergo scission, (c) in benzenesulfonylthioureas substituted by

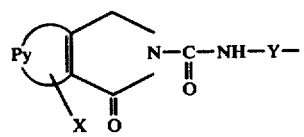

the sulfur atom is replaced by oxygen,
(d) corresponding benzenesulfinyl-ureas or -sulfenylureas are oxidized,
(e) the radical

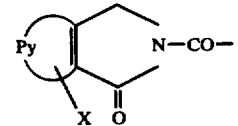

is introduced, if appropriate stepwise, into benzenesulfonylureas of the formula

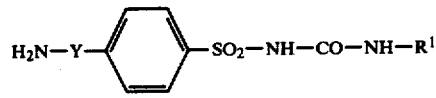

or
(f) correspondingly substituted benzenesulfonyl halides are reacted with $R^1$-substituted ureas or their alkali metal salts or correspondingly substituted benzenesulfinic acid halides or, in the presence of acid condensation agents, also correspondingly substituted sulfinic acids or their alkali metal salts, are reacted with N-$R^1$-N'-hydroxy-urea and, if desired, the reaction products are treated with alkaline agents in order to form the salts.

The benzenesulfonyl-carbamic acid esters and -thiolcarbamic acid esters which have been mentioned can contain an alkyl radical or an aryl radical, or even a heterocyclic radical, in the alcohol component. Since this radical is split off during the reaction, its chemical structure has no influence on the character of the end product and can therefore be varied within wide limits. The same is true of the N-$R^1$-substituted carbamic acid esters and the corresponding thiolcarbamic acid esters.

Suitable carbamic acid halides are above all the chlorides.

The benzenesulfonylureas which may be used as starting materials for the process can be unsubstituted, monosubstituted or, in particular, disubstituted on the side of the urea molecule opposite from that carrying the sulfonyl group. Since these substituents are split off during the reaction with amines, their character can be varied within wide limits. In addition to benzenesulfonylureas substituted by alkyl, aryl, acyl or a heterocycle, it is also possible to use benzenesulfonylcarbamoylimidazoles and similar compounds or bisbenzenesulfonylureas which on one of the nitrogen atoms can carry a further substituent, for example methyl. For example, such bis(benzenesulfonyl)-ureas or N-benzenesulfonyl-N'acylureas can be treated with $R^1$-substituted amines and the resulting salts can be heated to elevated temperatures, especially to temperatures above 100° C.

Furthermore, it is possible to start from $R^1$-substituted ureas, or from those $R^1$-substituted ureas which are additionally monosubstituted or, in particular, disubstituted at the free nitrogen atom, and to react these with benzenesulfonamides substituted by

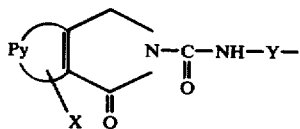

in the 4-position. Examples of possible starting materials of this type are N-cyclohexyl-urea, the corresponding N'-acetyl-, N'-nitro-, N'-cyclohexyl-, N',N'-diphenyl-, (it being possible for the two phenyl radicals also to be substituted and to be bonded to one another either directly or via a bridge member such as —CH₂—, —NH—, —O— or —S—), N'-methyl-N'-phenyl- and N',N'-dicyclohexylureas as well as cyclohexyl-carbamoyl-imidazoles, -pyrazoles or -triazoles, and those of the compounds mentioned, which instead of cyclohexyl, carry some other substituent falling within the range of definition of $R^1$.

The scission of the benzenesulfonylparabanic acids, -isourea ethers, -isothiourea ethers or -haloformamidines mentioned as starting materials in process (b) is advantageously effected by alkaline hydrolysis. Isourea ethers can also be very successfully subjected to scission in an acid medium.

The replacement of the sulfur atom in the thiourea grouping of correspondingly substituted benzenesulfonylthioureas by an oxygen atom can be effected in a known manner, for example with the aid of oxides or salts of heavy metals or by using oxidizing agents, such as hydrogen peroxide, sodium peroxide, nitrous acid or permanganates. The thioureas can also be desulfurized by treatment with phosgene or phosphorus pentachloride. Chloroformamidines or carbodiimides obtained as intermediates can be converted into the benzenesulfonylureas by suitable measures such as saponification or addition reaction with water.

The oxidation of benzenesulfinylureas or benzenesulfenylureas is carried out in accordance with a method which is in itself known, preferably with oxidizing agents such as permanganate or hydrogen peroxide.

The acylation of the sulfonylureas according to process (e) can be carried out with reactive derivatives of the acid

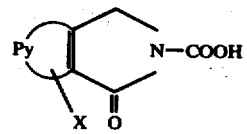

such as, for example, halides or urethans.

Suitable sulfonyl halides and sulfinyl halides for use in process (f) are in particular the chlorides. The acid condensation agent employed can be, for example, thionyl chloride or polyphosphoric acid.

The physiologically acceptable salts are manufactured in accordance with methods which are in themselves known. In particular, alkali metal and alkaline earth metal hydroxides, carbonates or bicarbonates, and physiologically tolerated organic bases, are suitable for forming salts.

The synthesis of the dihydropyrrolopyridines is carried out according to processes of the prior art (cf., for example, Chem. Ber. 82, page 36 (1949), Chem. Ber. 105, page 3611 (1972)) or in analogous manner thereto.

The embodiments of the process according to the invention can in general be varied substantially in respect to the reaction conditions and be suited to the particular circumstances. For example, the reactions can be carried out in the absence or presence of solvents, at room temperature or at an elevated temperature.

Depending on the character of the starting materials, one or other of the processes described can, in some cases, give a desired individual benzenesulfonylurea only in a low yield, or can be unsuitable for its synthesis. In such relatively rarely occuring cases it presents no difficulties to an expert to synthesize the desired product by another of the methods described.

The compounds obtained can be purified by reprecipitation and/or recrystallization. Alternatively, purification is also possible by liberating the substance from a crystalline (alkali metal) salt by means of a suitable solvent.

The compounds according to the invention are distinguished by valuable pharmacological properties, especially blood sugar-lowering properties. They are therefore suitable for use as medicaments, especially an antidiabetics.

The blood sugar-lowering action of the benzenesulfonylureas described can be ascertained by feeding them as the free compounds, or in the form of the sodium salts to rabbits which have received normal nutrition, in doses of 10 mg or 2 mg, respectively, per kg of body weight, and determining the blood sugar value by the known Hagedorn-Jensen method, or by means of an auto-analyzer, over a fairly long period of time.

The blood sugar-lowering action can alternatively be determined by using smaller doses or by applying other known methods.

The following compounds I to III were administered orally to rabbits in doses of 2 mg/kg and the blood sugar values were determined by means of an auto-analyzer over a fairly long period of time. The lowering of the blood sugar, thus measured, is shown in the table below in % after 1, 3, 6, 24, 48 and 72 hours.

I  N-(4-[2-(5-Oxo-6,7-dihydro-5H-pyrrolo-[3,4-b]-pyridin-6-yl-carboxamido)-ethyl]-benzenesulfonyl)-N'-(4-methyl-cyclohexyl)-urea II N-(4-[2-(5-Oxo-6,7-dihydro-5H-pyrrolo-[3,4-b]-pyridin-6-yl-carboxamido)-ethyl]-benzenesulfonyl)-N'-(4-ethyl-cyclohexyl)-urea III N-(4-[2-(5-Oxo-6,7-dihydro-5H-pyrrolo-[3,4-b]-pyridin-6-yl-carboxamide)-ethyl]-benzenesulfonyl)-N'-bicyclo[2.2.1]hept-2-yl-methyl-urea.

| Compound | Lowering of blood sugar in rabbits after oral administration of 2 mg/kg in % after | | | | | |
|---|---|---|---|---|---|---|
|  | 1 | 3 | 6 | 24 | 48/72 | hours |
| I |  | 31 | 34 | 36 | 19/0 |  |
| II | 36 | 52 | 54 | 48 | 38/0 |  |
| III | 43 | 26 | 38 | 26 | 0 |  |

The acylureido-alkylbenzenesulfonylureas according to the invention are distinguished by a pronounced and long-lasting blood sugar-lowering action.

The properties of the compounds make it possible to manage with such low doses in the therapy of diabetes mellitus that the preparation merely re-normalizes the reduced response capacity of the pancreas to an increased blood sugar level.

Benzenesulfonylureas containing a ureidoalkyl radical have already been described on several occasions (German Pat. No. 1,443,911, German Auslegeschrift No. 1,670,700; German Pat. Nos. 1,618,389 and 2,238,870). It was not to be expected that the compounds according to the invention would be distinguished by the advantageous properties mentioned above.

The sulfonylureas described are preferentially intended for the manufacture of orally administrable preparations for the treatment of patients suffering from or afflicted with diabetes mellitus. They can be administered as such or in the form of their salts or in the presence of material which lead to salt formation. For example, alkaline agents, such as alkali metal or alkaline earth metal hydroxides, carbonates or bicarbonates may be employed for forming salts. In addition to the sulfonylurea or its salt, the preparations can also contain other active compounds.

Suitable medicinal preparations are preferably tablets which in addition to the products of the process contain the customary excipients and auxiliaries such as talc, starch, lactose or magnesium stearate. A preparation which contains the described benzenesulfonylureas as the active compound, for example a tablet or a powder, with or without additives, is advantageously converted to a suitably dosed form. The dose to be selected in this context is such as to suit the activity of the benzenesulfonylurea employed and to suit the desired effect. Advantageously, the dosage per unit is about 0.1 to 10 mg, preferably 0.5 to 2 mg, but dosage units above or below this, which may have to be divided before administration or of which several may have to be taken, can also be used.

The examples which follow show some of the numerous process variants which can be used for the synthesis of the sulfonylureas according to the invention. They are, however, not intended to imply a limitation of the subject of the invention.

EXAMPLE 1

N-(4-[2-(5-Oxo-6,7-dihydro-5H-pyrrolo-[3,4-b]pyridin-6-yl-carboxamido)-ethyl]-benzenesulfonyl-N'-cyclohexyl-urea 1.8 g of 4-(2-[5-oxo-6,7-dihydro-5H-pyrrolo-[3,4-b]pyridin-6-yl-carboxamido]benzenesulfonamide of melting point 250°–252° C., which has been prepared by reacting 5-oxo-6,7-dihydro-5H-pyrrolo-[3,4-b]-pyridin-6-yl-(N-2-phenylethyl)-carboxamide (melting point 147° C., prepared from 6,7-dihydro-5H-pyrrolo-[3,4-b]pyridin-5-one and phenylethyl isocyanate) with chlorosulfonic acid and subsequent reaction of the sulfochloride obtained with ammonia, are refluxed for several hours, while stirring, in 80 ml of acetone after addition of 1.4 g of ground pottash. 0.7 g of cyclohecyl isocyanate, dissolved in a small amount of acetone, are added dropwise and the mixture is refluxed for a further 4 hours. After cooling, the acetone is distilled off in vacuo, the residue is dissolved in water and the pH of the resultant solution is adjusted to 3–4 with dilute hydrochloric acid. The precipitated sulfonylurea is reprecipitated from dilute ammonia solution with dilute hydrochloric acid and recrystallized from ethanol. This gives N-(4-[2-(5-Oxo-6,7-dihydro-5H-pyrrolo-[3,4-b]-pyridin-6-yl-carboxamido)-ethyl]-benzenesulfonyl)-N'-cyclohexylurea of melting point 222°–223° C.

The following compounds are obtained analogously:

N-(4-[2-(5-Oxo-6,7-dihydro-5H-pyrrolo-[3,4-b]-pyridin-6-yl-carboxamido)-ethyl]-benzenesulfonyl)-N'-(4-methyl-cyclohexyl)-urea of melting point 226° C. (from ethanol), N-(4-[2-(5-Oxo-6,7-dihydro-5H-pyrrolo-[3,4-b]-pyridin-6-yl-carboxamido)-ethyl]-benzenesulfonyl)-N'-(4-ethyl-cyclohexyl)-urea of melting point 226° C. (from ethanol)

N-(4-[2-(5-Oxo-6,7-dihydro-5H-pyrrolo-[3,4-b]-pyridin-6-yl-carboxamido)-ethyl]-benzenesulfonyl)-N'-($\Delta^3$-cyclohexenyl)-urea of m.p. 230°–232° C. (from ethanol-dimethylformamide)

N-(4-[2-(5Oxo-6,7-dihydro-5H-pyrrolo-[3,4-b]-pyridin-6-yl-carboxamido)-ethyl]-benzenesulfonyl)-N'-n-hexyl-urea of m.p. 183° C. (from ethanol)

N-(4-[2-(5-Oxo-6,7-dihydro-5H-pyrrolo-[3,4-b]-pyridin-6-yl-carboxamido)-ethyl]-benzensulfonyl)-N'-cyclopentyl-urea of m.p. 216°–217° C. (from ethanol)

N-(4-[2-(5-Oxo-6,7-dihydro-5H-pyrrolo-[3,4-b]-pyridin-6-yl-carboxamido)-ethyl]-benzenesulfonyl)-N'-bicyclo[2.2.1]-hept-2-yl-methyl-urea of m.p. 240°–241° C. (from ethanol-dimethylformamide)

N-(4-[2-(5-Oxo-6,7-dihydro-5H-pyrrolo-[3,4-b]-pyridin-6-yl-carboxamido)-ethyl]-benzenesulfonyl)-N'-cyclopentylmethyl-urea of m.p. 210°–211° C. (from ethanol)

N-(4-[2-(5-Oxo-6,7-dihydro-5H-pyrrolo-[3,4-b]-pyridin-6-yl-carboxamido)-ethyl]-benzensulfonyl)-N'-(3-methyl-cyclopentylmethyl)-urea of m.p. 186°–188° C. (from ethanol).

EXAMPLE 2

N-(4-[2-Oxo-2,3-dihydro-6-methyl-1H-pyrrolo-[3,4-c]-pyridin-2-yl-carboxamido)-ethyl]-benzenesulfonyl)-N'-cyclohexyl-urea 1.9 g of 4-(2-[1-oxo-2,3-dihydro-6-methyl-1H-pyrrolo-[3,4-c]-pyridin-2-yl-carboxamido]-ethyl)-benzenesulfonamide of melting point 225° C., which has been prepared by reacting 1-oxo-2,3-dihydro-6-methyl-1H- pyrrolo-[3,4-c]-pyridin-2-yl-(N-2-phenylethyl)-carboxamide [melting point 163°-165° C., prepared from 2-methyl-5-aminomethyl-isonicotinic acid lactam and phenylethyl isocyanate] with chlorosulfonic acid and subsequent reaction of the resulting sulfochloride with ammonia, are heated to the boil while stirring for 5 hours in 80 ml of acetone, after addition of 1.4 g of ground pottash. After addition of 0.7 g of cyclohexyl isocyanate in a small amount of acetone, the mixture is stirred for a further 4 hours at the boil. The cooled suspension is concentrated by evaporation in vacuo and the residue is dissolved in water, filtered and acidified to pH 3–4 with dilute hydrochloric acid. The precipitated N-(4-[2-(1-oxo-2,3-dihydro-6-methyl-1H-pyrrolo-[3,4-c]-pyridin-2-yl-carboxamido)-ethyl]-benzenesulfonyl)-N'-cyclohexyl-urea is precipitated from dilute ammonia solution with dilute hydrochloric acid and subsequently recrystallized from ethanol. Melting point 228° C.

The following compound is obtained analogously:

N-(4-[2-(1-Oxo-2,3-dihydro-6-methyl-1H-pyrrolo-[3,4-c]-pyridin-2-yl-carboxamido)-ethyl]-benzenesulfonyl)-N'-(4-methyl-cyclohexyl)-urea of m.p. 206° C. (from ethanol).

EXAMPLE 3

N-(4-[2-(3-Oxo-2,3-dihydro-1H-pyrrolo-[3,4-c]-pyridin-2-yl-carboxamido)-ethyl]-benzenesulfonyl)-N'-cyclohexyl-urea 0.9 g of 4-(2-[3-oxo-2,3-dihydro-1H-pyrrolo-[3,4-c]-pyridin-2-yl-carboxamido)-ethyl]-benzenesulfonamide of melting point 258°-260° C., which has been prepared by reacting 3-oxo-2,3-dihydro-1H-pyrrolo-[3,4-C]-pyridin-2-yl-(N-2-phenylethyl)-carboxamide (melting point 198°-200° C., prepared from 2,3-dihydro-1H-pyrrolo-[3,4-C]-pyridin-3-one and 2-phenylethyl isocyanate) with chlorosulfonic acid and reaction of the resultant sulfochloride with ammonia, are refluxed for 6 hours in 50 ml of acetone after addition of 0.7 g of ground pottash. After cooling, 0.3 g of cyclohexyl isocyanate, dissolved in a small amount of acetone, is added and the mixture is stirred at the boil for a further 4 hours. The suspension is concentrated by evaporation in vacuo, the residue is dissolved in water, filtered and acidified with dilute acetic acid. The precipitate is filtered off with suction, reprecipitated from dilute ammonia solution with dilute acetic acid and recrystallized from ethyl/-dimethylformamide. The N-(4-[2-(3-oxo-2,3-dihydro-1H-pyrrolo-[3,4-C]-pyridin-2-yl-carboxamido)-ethyl]-benzenesulfonyl)-N'-cyclohexyl urea obtained melts at 224°-226° C.

The following compounds are obtained analogously:

N-(4-[2-(3-Oxo-2,3-dihydro-1H-pyrrolo-[3,4-C]-pyridin-2-yl-carboxamido)-ethyl]-benzenesulfonyl)-N'-(4-methyl-cyclohexyl)-urea of m.p. 224°-225° C. (from ethanol)

N-(4-[2-(3-Oxo-2,3-dihydro-1H-pyrrolo-[3,4-C]-pyridin-2-yl-carboxamido)-ethyl]-benzenesulfonyl)-N'-butyl-urea of m.p. 209°-211° C. (from ethanol)

EXAMPLE 4

N-(4-[2-(7-Oxo-5,6-dihydro-7H-pyrrolo-[3,4-b]-pyridin-6-yl-carboxamido)-ethyl]-benzenesulfonyl)-N'-cyclohexyl-urea 1.8 g of 4-(2-[7-oxo-5,6-dihydro-5H-pyrrolo-[3,4-b]-pyridin-6-yl-carboxamido)-ethyl]-benzenesulfonamide of melting point 248°-251°, which has been prepared by reacting 7-oxo-5,6-dihydro-7H-pyrrolo-[3,4-b]-pyridin-2-yl-(N-2-phenyl-ethyl)-carboxamide (melting point 172°-173° C., prepared from 5,6-dihydro-7H-pyrrolo-[3,4-b]-pyridin-7-one and 2-phenylethyl isocyanate) with chlorosulfonic acid and subsequent reaction of the sulfochloride obtained with ammonia, are suspended in 75 ml of butanone-2 with 1.4 g of ground pottash and after addition of 0.65 g of cyclohexyl isocyanate stirred at the boil. The solvent is distilled off, the residue is dissolved in water and the resultant solution is acidified with dilute acetic acid. The precipitate is filtered off, reprecipitated from dilute acetic acid and recrystallized from ethanol, which gives N-(4-[2-(7-oxo-5,6-dihydro-7H-pyrrolo-[3,4-b]-pyridin-6-yl-carboxamido)-ethyl]-benzene-sulfonyl)-N'-cyclohexyl-urea of melting point 220°-221° C.

The following compounds are obtained analogously:

N-(4-[2-(7-Oxo-5,6-dihydro-7H-pyrrolo-[3,4-b]-pyridin-6-yl-carboxamido)-ethyl]-benzenesulfonyl)-N'-butyl-urea of m.p. 219°-220° C. (from ethanol)

N-(4-[2-(7-Oxo-5,6-dihydro-7H-pyrrolo-[3,4-b]-pyridin-6-yl-carboxamido)-ethyl]-benzenesulfonyl)-N'-(4-methyl-cyclohexyl)-urea of m.p. 227°-228° C. (from ethanol)

N-(4-[2-(7-Oxo-5,6-dihydro-7H-pyrrolo-[3,4-b]-pyridin-6-yl-carboxamido)-ethyl]-benzenesulfonyl)-N'-(3-methyl-cyclopentylmethyl)-urea of m.p. 230°-231° C. (from ethanol)

EXAMPLE 5

N-(4-[2-(5-Oxo-6,7-dihydro-5H-pyrrolo-[3,4-b]-pyridin-6-yl-carboxamido)-ethyl]-benzenesulfonyl)-N'-cyclohexyl-urea 1.08 g of N-(4-(2-[5-oxo-6,7-dihydro-5H-pyrrolo-[3,4-b]-pyridin-6-yl-carboxamido)-ethyl]-benzenesulfonyl)-N'-cyclohexyl-thiourea (melting point 208°-210° C., prepared from the corresponding sulfonamide and cyclohexyl mustard oil) are heated at the boil while stirring in 75 ml of water and 75 ml of methanol after addition of 0.64 g of yellow mercury oxide. After cooling, the mercury sulfide is filtered off, the filtrate is concentrated by evaporation in vacuo and the residue is crystallized from ethanol. The resulting N-(4-[2-(5-oxo-6,7-dihydro-5H-pyrrolo-[3,4-b]-pyridin-6-yl-carboxamido)-ethyl]-benzenesulfonyl)-N'-cyclohexyl-urea melts at 221°-223° C.

EXAMPLE 6

N-(4-[2-(5-Oxo-6,7-dihydro-5H-pyrrolo-[3,4-b]-pyridin-6-yl-carboxamido)-ethyl]-benzenesulfonyl)-N'-cyclohexyl-urea 1.08 g of N-(4-(2-[5-oxo-6,7-dihydro-5H-pyrrolo-[3,4-b]-pyridin-6-yl-carboxamido)-ethyl]-benzenesulfonyl)-N'-cyclohexyl-thiourea (melting point 208°-210° C., prepared from the corresponding sulfonamide and cyclohexyl mustard oil) are heated at the boil while stirring for several hours, in 75 ml of anhydrous methanol, after addition of 0.64 g of yellow mercury oxide. After cooling, the mercury sulfide is filtered off and the filtrate is concentrated by evaporation leaving N-(4-[2-(5-oxo-6,7-dihydro-5H-pyrrolo-[3,4-b]-pyridin-6-yl-carboxamido)-ethyl]-benzenesulfonyl)-N'-cyclohexyl-isourea-methyl ether. This crude product is stirred for 2 hours at 50° C. in 30 ml of concentrated hydrochloric acid, diluted with 30 ml of water and adjusted to pH 3-4. The N-(4-[2-(5-oxo-6,7-dihydro-5H-pyrrolo-[3,4-b]-pyridin-6-yl-carboxamido)-ethyl]-benzenesulfonyl)-N'-cyclohexyl-urea which has precipitated during crys-

EXAMPLE 7

N-(4-[2-(5-Oxo-6,7-dihydro-5H-pyrrolo-[3,4-b]-pyridin-6-yl-carboxamido)-ethyl]-benzenesulfonyl)-N'-cyclohexyl-urea 1.52 g (0.01 mol) of cyclohexyl-urea are heated at the boil while stirring for 3 hours in 50 ml of tetrahydrofurane after addition of 0.6 g of a 55% dispersion of sodium hydride. After cooling, there is added dropwise a solution of 3.8 g of 4-[2-(5-oxo-6,7-dihydro-5H-pyrrolo-[3,4-b]-pyridin-6-yl-carboxamido)-ethyl]-benzenesulfonic acid chloride (prepared in the manner described in Example 1) in 20 ml of tetrahydrofurane. The product is heated at the boil for a further 3 hours. After cooling, the precipitate is filtered off with suction, dissolved in water and acidified to pH 3–4. A subsequent reprecipitation from dilute ammonia solution with dilute hydrochloric acid and recrystallization from ethanol yields N-(4-[2-(5-oxo-6,7-dihydro-5H-pyrrolo-[3,4-b]-pyridin-6-yl-carboxamido)-ethyl]-benzenesulfonyl)-N'-cyclohexyl-urea of melting point 222°–223° C.

EXAMPLE 8

N-(4-[2-(5-Oxo-6,7-dihydro-5H-pyrrolo-[3,4-b]-pyridin-6-yl-carboxamido)-ethyl]-benzenesulfonyl)-N'-cyclohexyl-urea To 2.01 g of 6,7-dihydro-5H-pyrrolo-[3,4b]pyridin-5-one in 50 ml of absolute toluene there is added 0.72 g of a 55% dispersion of sodium hydride in paraffin and the mixture is heated at the boil while stirring for 6 hours. After cooling, there is added 15 ml of a 25% phosgene solution in toluene and the product is stirred for a further 3 hours at 50° C. The resulting solution of carbamoyl chloride is filtered and added dropwise at room temperature to a suspension of 3.16 g of N-(4-[2-aminoethyl]-benzenesulfonyl)-N'-cyclohexyl-urea and 2.8 ml of triethylamine in 50 ml of tetrahydrofurane. The product is stirred for 3 hours at room temperature, while keeping its pH in an alkaline range. The product is concentrated in vacuo, the residue is reprecipitated from dilute ammonia solution with dilute acetic acid and recrystallized from ethanol. The N-(4-[2-(5-oxo-6,7-dihydro-5H-pyrrolo-[3,4-b]-pyridin-6-yl-carboxamido)-ethyl]-benzenesulfonyl)-N'-cyclohexyl-urea does not differ from a sample prepared according to Example 1, with respect to an analysis by thin layer chromatography and to the mixed melting point with this sample.

EXAMPLE 9

N-(4-[2-(5-Oxo-6,7-dihydro-5H-pyrrolo-[3,4-b]-pyridin-6-yl-carboxamido)-ethyl]-benzenesulfonyl)-N'-cyclohexyl-urea 2.01 g of N-(4-[2-(5-oxo-6,7-dihydro-5H-pyrrolo-[3,4-b]-pyridin-6-yl-carboxamido)-ethyl]-benzenesulfonyl)-urea (melting point 243°–245° C., prepared from the corresponding benzensulfonamide and potassium cyanate) are heated to the boil while stirring for 3 hours in 50 ml of dioxane after addition of 1.03 g of cyclohexylamine. While cooling, a colorless precipitate is formed, which is suction filtered, suspended in 50 ml of water and acidified with dilute acetic acid. The resulting N-(4-[2-(5-oxo-6,7-dihydro-5H-pyrrolo-[3,4-b]-pyridin-6-yl-carboxamido)-ethyl]-benzenesulfonyl)-N'-cyclohexyl-urea is suction-filtered and recrystallized from ethanol/-dimethylformamide. The melting point is 220°–222° C.

This product corresponds to the sample prepared in Example 1, as shown by thin layer chromatography and by its mixed melting point with this sample.

The following compounds are obtained analogously:

N-(4-[2-(5-Oxo-6,7-dihydro-5H-pyrrolo-[3,4-b]-pyridin-6-yl-carboxamido)-ethyl]-benzenesulfonyl)-N'-(4-chlorocyclohexyl)-urea of m.p. 220°–221° C. (from ethanol-dimethylformamide)

N-(4-[2-(5-Oxo-6,7-dihydro-5H-pyrrolo-[3,4-b]-pyridin-6-yl-carboxamido)-ethyl]-benzenesulfonyl)-N'-(4-methoxy-cyclohexyl)-urea of m.p. 190°–192° C. (from acetic ester)

EXAMPLE 10

N-(4-[2-(5-Oxo-2,3-dihydro-5H-pyrrolo-[3,4-b]-pyridin-6-yl-carboxamido)-ethyl]-benzenesulfonyl)-N'-cyclohexyl-urea Over 6.9 g (0.02 mol) of 4-(2-[5-oxo-2,3-dihydro-5H-pyrrolo-[3,4-b]-pyridin-6-yl-carboxamido]-ethyl)-benzenesulfinic acid of melting point 253°–255° C. (with decomposition), which has been prepared from 5-oxo-2,3-dihydro-5H-pyrrolo-[3,4-b]-pyridin-2-yl-(N-2-phenylethyl)-carboxamide (melting point 147°–148° C., prepared from 2,3-dihydro-5H-pyrrolo-[3,4-b]-pyridin-5-one and 2-phenylethyl-isocyanate) and chlorosulfonic acid and subsequent reaction of the resulting sulfochloride with sodium sulfide in chloroform and water, there is poured 7.2 ml of thionyl chloride. The sulfinyl chloride isolated by suction-filtration is reacted with cyclohexylurea in pyridine yielding N-(4-[2-(5-oxo-2,3-dihydro-5H-pyrrolo-[3,4-b]-pyridin-6-yl-carboxamido)-ethyl]-benzenesulfinyl)-N'-cyclohexyl-urea. Oxidation with permanganate in dimethylformamide yields N-(4-[2-(5-oxo-2,3-dihydro-5H-pyrrolo-[3,4-b]-pyridin-6-yl-carboxamido)-ethyl]-benzenesulfonyl)-N'-cyclohexyl-urea of melting point 221°–223° C.

What is claimed is:

1. A compound of the formula

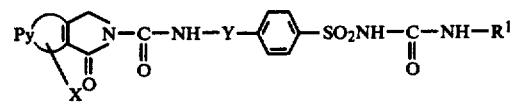

or a physiologically acceptable salt thereof in which $$Py$$

is a fused pyridine ring in which the nitrogen atom is in any of the four possible positions;

X is hydrogen, alkyl of 1 to 4 C atoms or halogen;

Y is alkylene of 2–3 C atoms; and $R^1$ is alkyl of 4 to 8 C atoms, cycloaklyl, alkylcycloalkyl, dialkylcycloalkyl, cycloalkylalkyl, cycloalkenyl or alkylcycloalkenyl, in each instance with 5–9 C atoms, methylcyclopentylmethyl, cyclohexenylmethyl, chlorocyclohexyl, methoxycyclohexyl, bicycloheptyl, bicycloheptenyl, bicycloheptylmethyl, bicycloheptenylmethyl, bicyclooctyl, nortricyclyl, adamantyl or benzyl.

2. The compound of claim 1 which is N-(4-[2-(5-Oxo-6,7-dihydro-5H-pyrrolo-[3,4-b]pyridin-6-yl-carboxamido)-ethyl]-benzenesulfonyl-N'-cyclohexyl-urea.

3. The compound of claim 1 which is N-(4-[2-(5-Oxo-6,7-dihydro-5H-pyrrolo-[3,4-b]-pyridin-6-yl-carboxamido)-ethyl]-benzenesulfonyl)-N'-(4-methyl-cyclohexyl)-urea.

4. The compound of claim 1 which is N-(4-[2-(5-Oxo-6,7-dihydro-5H-pyrrolo-[3,4-b]-pyridine-6-yl-carboxamido)-ethyl]-benzenesulfonyl)-N'-(4-ethyl-cyclohexyl)-urea.

5. The compound of claim 1 which is N-(4-[2-(5-Oxo-6,7-dihydro-5H-pyrrolo-[3,4-b]-pyridin-6-yl-carboxamido)-ethyl]-benzenesulfonyl)-N'-bicyclo[2.2.1]hept-2-yl-methyl urea.

6. An oral antidiabetic composition comprising a hypoglycemically effective amount of a compound as defined in claim 1 and a customary excipient or auxiliary.

7. A method of treatment of hyperglycemia which comprises administering to a diabetic a hypoglycemically effective amount of a compound as defined in claim 1.